(12) United States Patent
Heitel et al.

(10) Patent No.: US 9,155,658 B2
(45) Date of Patent: Oct. 13, 2015

(54) SYSTEMS AND METHODS FOR DYNAMIC PATIENT FIXATION SYSTEM

(71) Applicant: AMO Development, LLC., Santa Ana, CA (US)

(72) Inventors: Robert Heitel, Laguna Beach, CA (US); Hong Fu, Irvine, CA (US)

(73) Assignee: AMO Development, LLC, Santa Ana, CA (US)

( * ) Notice: Subject to any disclaimer, the term of this patent is extended or adjusted under 35 U.S.C. 154(b) by 10 days.

(21) Appl. No.: 14/146,090

(22) Filed: Jan. 2, 2014

(65) Prior Publication Data

US 2014/0218689 A1  Aug. 7, 2014

Related U.S. Application Data

(60) Provisional application No. 61/748,365, filed on Jan. 2, 2013.

(51) Int. Cl.
 *A61B 3/10* (2006.01)
 *A61B 3/14* (2006.01)
 *A61F 9/008* (2006.01)

(52) U.S. Cl.
 CPC ....... *A61F 9/008* (2013.01); *A61F 2009/00846* (2013.01)

(58) Field of Classification Search
 USPC .................................................. 351/200–246
 See application file for complete search history.

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,732,148 A | 3/1988 | L'Esperance, Jr. | |
| 4,764,930 A | 8/1988 | Bille et al. | |
| 4,770,172 A | 9/1988 | L'Esperance, Jr. | |
| 4,773,414 A | 9/1988 | L'Esperance, Jr. | |
| 5,108,388 A | 4/1992 | Trokel | |
| 5,163,934 A | 11/1992 | Munnerlyn | |
| 5,207,668 A | 5/1993 | L'Esperance, Jr. | |
| 5,219,343 A | 6/1993 | L'Esperance, Jr. | |
| 5,646,791 A | 7/1997 | Glockler | |
| 5,980,513 A * | 11/1999 | Frey et al. ....................... | 606/10 |
| 5,993,438 A | 11/1999 | Juhasz et al. | |
| 6,299,307 B1 | 10/2001 | Oltean et al. | |
| 6,406,473 B1 | 6/2002 | Shimmick et al. | |
| 6,663,619 B2 * | 12/2003 | Odrich et al. ..................... | 606/5 |
| 2004/0243111 A1 | 12/2004 | Bendett et al. | |

* cited by examiner

*Primary Examiner* — Mohammed Hasan
(74) *Attorney, Agent, or Firm* — Abbott Medical Optics Inc.

(57) ABSTRACT

The field of the invention relates to systems and methods for ophthalmic laser procedure and, more particularly, to systems and methods for dynamic fixation used in the fixation of the eye(s) of a patient during laser-assisted ophthalmic surgery and/or ophthalmic diagnostic and measurement systems where visualization and concentration on a target are desired. The invention generally enhances the alignment between the eye and a laser beam of a laser eye surgery system using visual fixation system and laser delivery optics. The visual fixation system allows a patient's eye(s) to be accurately focused at one or more fixation targets.

5 Claims, 6 Drawing Sheets

SYSTEMS AND METHODS FOR DYNAMIC PATIENT FIXATION SYSTEM

CROSS REFERENCE TO RELATED APPLICATIONS

This application claims the benefit of priority to U.S. Provisional Application No. 61/748,365, filed Jan. 2, 2013, the entirety of which is incorporated herein by reference.

FIELD OF THE INVENTION

The present invention generally relates to laser-assisted ophthalmic procedures and, more particularly, to systems and methods for dynamic fixation used in the fixation of the eye(s) of a patient during laser-assisted ophthalmic surgery and/or for ophthalmic diagnostic and measurement procedures where visualization and concentration on a target are desired.

BACKGROUND OF THE INVENTION

With recent significant developments in laser technology and its application in the field of ophthalmology, laser surgery has become the technique of choice for ophthalmic surgical applications, such as refractive surgery for correcting myopia, hyperopia, astigmatism, and so on, and procedures for treating and removing a cataractous lens. Laser eye surgery procedures generally employ an ultraviolet, an infrared, or a non-ultraviolet, ultrashort pulsed laser beam, and are performed while the patient is awake. The patient's head is stabilized using a headrest pillow, or the like. The laser surgical procedure typically requires that the patient's eye movement be stabilized. One approach to stabilize eye movement is to have the patient focus on a target during the procedure. These visual fixation targets typically include a light emitting diode (LED), which is optically positioned in front of or above the patient. Eye tracking systems have also been proposed to assist in eye fixation. Various systems and methods have been described for eye fixation, and separately for tracking eye movements. U.S. Pat. No. 6,299,307 issued to Oltean et al. discloses techniques for tracking eye movements. U.S. Pat. No. 6,406,473 issued to Shimmick et al. discloses techniques for providing eye fixation. These patents are herein incorporated by reference in their entirety.

It is desired that, when eye tracking is used, the patient interface be eliminated. The patient interface used in laser surgery is typically a rigid (glass lens) or a fluid (Balanced Salt Solution or "BSS") interface comprised of a metal or rigid plastic conical adapter. The large end of the cone is a laser (fixation) mount. The small end of the cone fits against the corneal or scleral region of the eye with the aid of suction pressure. Instead of using such patient interface, it is desired that the eye be tracked using an eye tracking camera of the eye tracking system. The eye tracking system would then monitor the position and movements of the patient's eye. In order for the surgical process to proceed and continue, however, the patient's eye must remain generally fixed within a small central orientation. If the eye wanders, for example, outside of a 5 degree central region, the operation has to be halted until the eye returns to the eye tracking system's capture range and the range within which the laser can be successfully administered.

Current eye tracking and fixation systems and methods typically describe a single point fixation, fixed fixation, and/or central illumination target. In a single point fixation technique, light energy is directed toward the eye as a beam of light energy. The intersection of the beam of light energy with the eye comprises a light spot formed on the eye. Another technique may use a beam splitter to direct a plurality of light spots on the eye. In these techniques, however, the light spot or spots formed on the eye are fixed, and typically converged in the central region of vision, where visual acuity is the greatest. However, there may be certain situations and procedures that may cause the eye to lose its focus on the desired fixed point, thereby causing the eye to shift into undesirable positions. For instance, during cataract surgery, where lens fragmentation is carried out, the fragmented lens may hinder the patient's ability to fixate on the original fixed light spot. As a result, the patient's familiarity with the surroundings is eliminated, and he or she may not be able to hold his or her eye steady or to look in the direction necessary for the surgery.

Accordingly, improved systems and methods for guiding a patient's eye fixation during a laser ophthalmic surgery and/or ophthalmic diagnostic and measurement are desirable.

SUMMARY OF THE INVENTION

The field of the invention relates to ophthalmic laser procedure and, more particularly, to systems and methods for dynamic fixation used in the fixation of the eye of a patient during laser-assisted ophthalmic surgery and/or ophthalmic diagnostic and measurement procedures where visualization and concentration on a target are desired. During an ophthalmic laser procedure, if the patient's eye is not rigidly fixed to the laser delivery system by some form of docking mechanism while being tracked by an eye tracking system, (as is typical in laser-assisted cataract surgery), then the probability of the patient's eye either voluntarily or involuntarily wandering to find familiar lighting will be much greater. In such a situation, the laser procedure will typically have to be paused or halted until the eye is re-centered enough for the eye tracking system to reestablish its target acquisition. With a dynamic fixation source, for example, variable fixation lighting, control of the patient's eye fixation may be increased throughout the procedure. In one embodiment, an ophthalmic laser-based treatment system may include a laser delivery system for delivering a pulsed laser beam to photoalter an eye, an eye fixation system configured to cause the eye to be fixated at a desired position, and an eye fixation adjustment system configured to enable the eye fixation system to be dynamically adjusted.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

In order to better appreciate how the above-recited and other advantages and objects of the inventions are obtained, a more particular description of the embodiments briefly described above will be rendered by reference to specific embodiments thereof, which are illustrated in the accompanying drawings. It should be noted that the components in the figures are not necessarily to scale, emphasis instead being placed upon illustrating the principles of the invention. Moreover, in the figures, like reference numerals designate corresponding parts throughout the different views. However, like parts do not always have like reference numerals. Moreover, all illustrations are intended to convey concepts, where relative sizes, shapes and other detailed attributes may be illustrated schematically rather than depicted literally or precisely.

DETAILED DESCRIPTION OF THE PREFERRED EMBODIMENTS

The present invention is generally directed to systems and methods for ophthalmic laser surgery and, more particularly, to systems and methods for dynamic fixation used in the fixation of a patient's eye during laser-assisted ophthalmic surgery and/or ophthalmic diagnostic and measurement procedures where visualization and concentration on a target are desired. The invention generally enhances the alignment between the eye and a laser beam of a laser-assisted eye surgery system using a visual fixation system and laser delivery optics. The visual fixation system allows an eye to be accurately focused at one or more fixation targets. The laser delivery optics project one or more images of the one or more targets so that the one or more images are selectively focused in front of, at, or behind the plane of the patient's eye.

In one embodiment, the present invention allows the patient to focus upon (and minimize misalignment with) one or more target images while the eye undergoes significant refractive changes. For example, a patient undergoing a photorefractive therapy for 4.0 D hyperopia will have a significant change in the refractive configuration of the eye during the therapy. To maintain alignment between the changing eye and the laser beam, the present invention encompasses dynamically varying or re-positioning the one or more target images and/or the image plane of the projected one or more target images. In another example, a patient undergoing a cataract surgery will have the cataractal lens ablated prior to removal. In this instance, the present invention encompasses dynamically varying or re-positioning the one or more images, for example, to outside of the cataractic lens area. As a result, during the therapy or surgery, the target image or images may be dynamically adjusted, changed, or re-positioned.

The target image or images may be dynamically adjusted, changed, or re-positioned by, for example, applying different or varying distances, or based on timing, movement of light source, frequency of blinking of the eye, or corneal sensitivity level, or in synchronization with the surgical procedure, or in response to or in synchronization with any other information received from the eye, and so on. The dynamic adjustments, changes or re-positions of the target image or images may be done automatically by a computer program or software, or by using input received from a system operator, who may be a surgeon performing the surgery.

Figure 1:
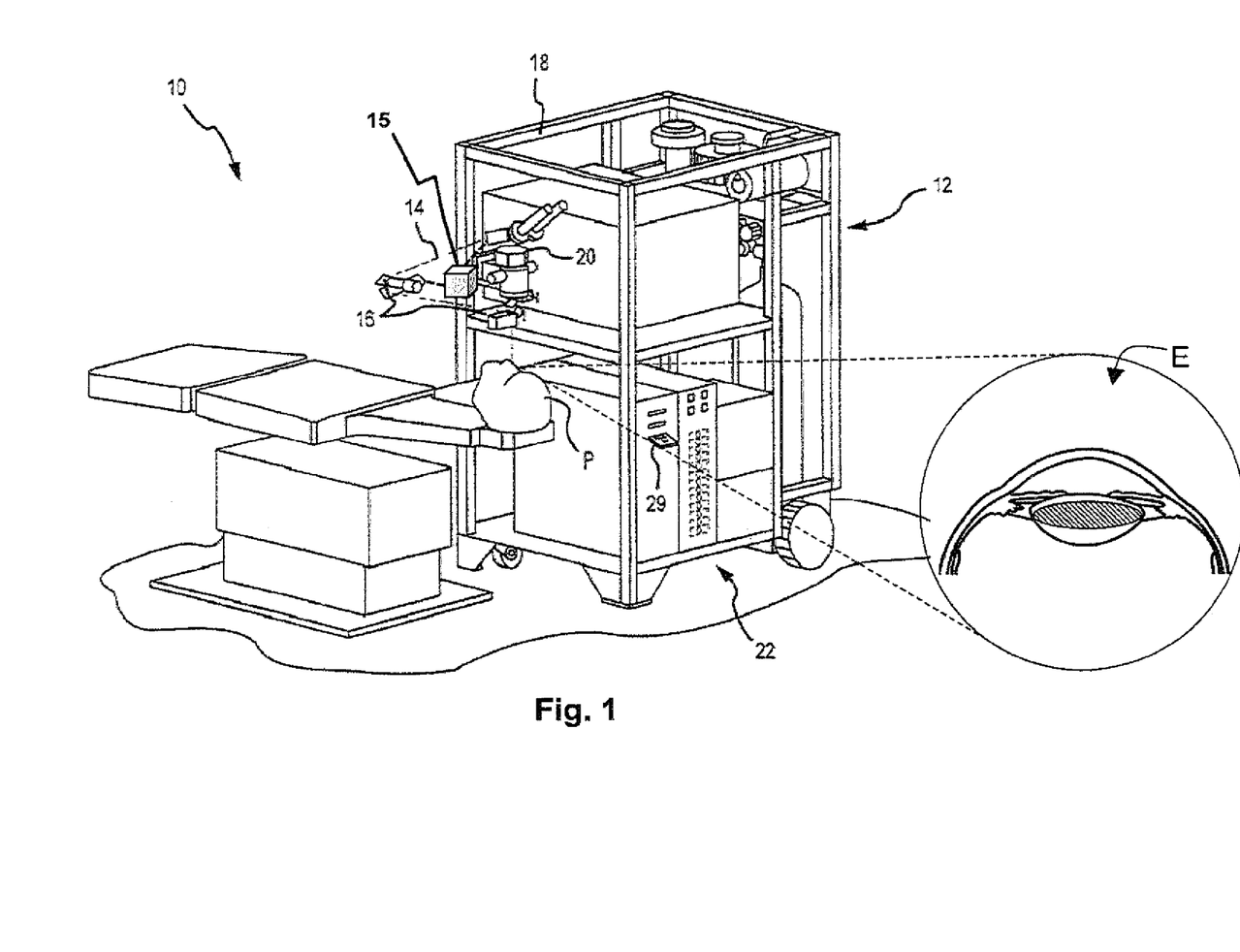
FIG. 1 is a perspective view of a laser eye surgery system according to a preferred embodiment of the present invention.

Turning to FIG. 1, an illustration of a laser eye surgery system 10 is shown. The laser system 10 includes a laser 12 that produces a laser beam 14 which generates laser beam pulses. Laser 12 is optically coupled to laser delivery optics 16, which, under the direction of a computer system 22, directs laser beam 14 to an eye E of patient P. A delivery optics support structure (not shown here for clarity) extends from a frame 18 supporting laser 12. A microscope 20 is mounted on the delivery optics support structure. A fixation system 15 is generally coupled to laser 12, laser delivery optics 16 and the delivery optics support structure. The fixation system 15 may also operate under the direction of computer system 22. Laser 12 may be designed to provide a feedback stabilized fluence at the patient's eye, delivered via delivery optics 16.

U.S. Pat. Publication No. 2004/0243111 describes methods of photoalteration, which is incorporated herein. Other devices or systems may also be used to generate pulsed laser beam 14. For example, non-ultraviolet (UV), ultrashort pulsed laser technology can produce pulsed laser beam 14 having pulse durations measured in femtoseconds. Some of the non-UV, ultrashort pulsed laser technology may be used in ophthalmic applications. For example, U.S. Pat. No. 5,993,438 discloses a device for performing ophthalmic surgical procedures to effect high-accuracy corrections of optical aberrations. U.S. Pat. No. 5,993,438 discloses an intrastromal photodisruption technique for reshaping the cornea using a non-UV, ultrashort (e.g., femtosecond pulse duration), pulsed laser beam that propagates through corneal tissue and is focused at a point below the surface of the cornea to photodisrupt stromal tissue at the focal point.

Although the laser system 10 may be used to photoalter a variety of materials (e.g., organic, inorganic, or a combination thereof), the laser system 10 is suitable for ophthalmic applications in one embodiment. In this case, the focusing optics direct the pulsed laser beam 14 toward an eye E (e.g., onto or into a cornea) for plasma mediated (e.g., non-UV) photoablation of superficial tissue, or into the stroma of the cornea for intrastromal photodisruption of tissue. In this embodiment, the laser system 10 may also include a lens to change the shape (e.g., flatten or curve) of the cornea prior to scanning the pulsed laser beam 14 toward the eye E. The laser system 10 is capable of generating the pulsed laser beam 14 with physical characteristics similar to those of the laser beams generated by a laser system disclosed in U.S. Pat. No. 4,764,930 and U.S. Pat. No. 5,993,438, the entire disclosures of which are incorporated herein by reference.

For example, the ophthalmic laser system 10 can produce an ultrashort pulsed laser beam 14 for use as an incising laser beam 14. This pulsed laser beam 14 preferably has laser pulses with durations as long as a few nanoseconds or as short as a few femtoseconds. For intrastromal photodisruption of the tissue, the pulsed laser beam 14 has a wavelength that permits the pulsed laser beam 14 to pass through the cornea without absorption by the corneal tissue. The wavelength of the pulsed laser beam 14 is generally in the range of about 3 μm to about 1.9 nm, preferably between about 400 nm to about 3000 nm, and the irradiance of the pulsed laser beam 14 for accomplishing photodisruption of stromal tissues at the focal point is typically greater than the threshold for optical breakdown of the tissue. Although a non-UV, ultrashort pulsed laser beam is described in this embodiment, the pulsed laser beam may have other pulse durations and different wavelengths in other embodiments.

Computer system 22 may comprise (or interface with) a conventional or special computer, e.g., PC, laptop, and so on, including the standard user interface devices such as a keyboard, a mouse, a touch pad, foot pedals, a joystick, a touch screen, an audio input, a display monitor, and the like. Computer system 22 typically includes an input device such as a magnetic or optical disk drive, or an input interface such as a USB connection, a wired and/or wireless network connection, or the like. Such input devices or interfaces are often used to download a computer executable code, to a storage media 29, embodying any of the methods of the present invention. Storage media 29 may take the form of an optical disk, a data tape, a volatile or non-volatile memory, RAM, or the like, and the computer system 22 includes the memory and other standard components of modern computer systems for storing and executing this code. Storage media 29 includes one or more fixation maps, and may optionally include a treatment map, and/or an ablation table. Storage media 29 may alternatively be remotely operatively coupled with computer system 22 via network connections such as LAN, the Internet, or via wireless methods such as WLAN, Bluetooth, or the like.

Additional components and subsystems may be included with laser system 10, as should be understood by those of skill in the art. For example, spatial and/or temporal integrators may be included to control the distribution of energy within the laser beam, as described in U.S. Pat. No. 5,646,791, the full disclosure of which is incorporated herein by reference. Ablation effluent evacuators/filters, aspirators, and other ancillary components of the laser surgery system are known in the art. Further details of suitable systems for performing a laser ablation procedure can be found in commonly assigned U.S. Pat. Nos. 4,665,913, 4,669,466, 4,732,148, 4,770,172, 4,773,414, 5,207,668, 5,108,388, 5,219,343, 5,646,791 and 5,163,934, the complete disclosures of which are incorporated herein by reference.

Figure 2:
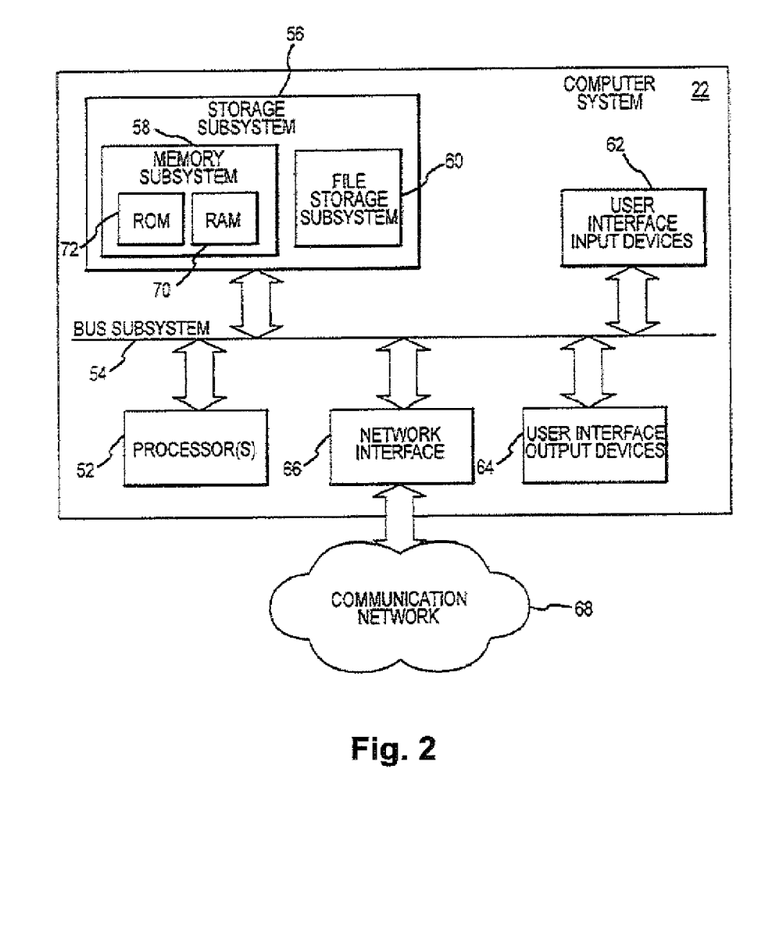
FIG. 2 is a simplified diagram of a computer system according to a preferred embodiment of the present invention.

FIG. 2 is a simplified block diagram of an exemplary computer system 22 that may be used by the laser surgical system 10 of the present invention. Computer system 22 typically includes at least one processor 52 which may communicate with a number of peripheral devices via a bus subsystem 54. These peripheral devices may include a storage subsystem 56, comprising a memory subsystem 58 and a file storage subsystem 60 (which may include storage media 29), user interface input devices 62, user interface output devices 64, and a network interface subsystem 66. Network interface subsystem 66 provides an interface to outside networks 68 and/or other devices.

User interface input devices 62 may include a keyboard, pointing devices such as a mouse, trackball, touch pad, or graphics tablet, a scanner, foot pedals, a joystick, a touchscreen incorporated into the display, audio input devices such as voice recognition systems, microphones, and other types of input devices. User interface input devices 62 are often used to download a computer executable code from a storage media 29 embodying any of the methods of the present invention. User interface input devices 62 are also used to control an eye fixation system. In general, use of the term "input device" is intended to include a variety of conventional and proprietary devices and ways to input information into computer system 22.

User interface output devices 64 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide a non-visual display such as via audio output devices. In general, use of the term "output device" is intended to include a variety of conventional and proprietary devices and ways to output information from computer system 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files, and may include storage media 29 (FIG. 1). File storage subsystem 60 may include a hard disk drive along with associated removable media, a Compact Disk (CD) drive, an optical drive, DVD, solid-state removable memory, and/or other removable media cartridges or disks. One or more of the drives may be located at remote locations on other connected computers at other sites coupled to computer system 22. The modules implementing the functionality of the present invention may be stored by file storage subsystem 60.

Bus subsystem 54 provides a mechanism for letting the various components and subsystems of computer system 22 communicate with each other as intended. The various subsystems and components of computer system 22 need not be at the same physical location but may be distributed at various locations within a distributed network. Although bus subsystem 54 is shown schematically as a single bus, alternate embodiments of the bus subsystem may use multiple busses.

Computer system 22 itself can be of varying types including a personal computer, a portable computer, a workstation, a computer terminal, a network computer, a control system in a wavefront measurement system or laser surgical system, a mainframe, or any other data processing system. Due to the ever-changing nature of computers and networks, the description of computer system 22 depicted in FIG. 2 is intended only as an example for purposes of illustrating one embodiment of the present invention. Many other configurations of computer system 22, having more or fewer components than the computer system depicted in FIG. 2, are possible.

Figure 3:
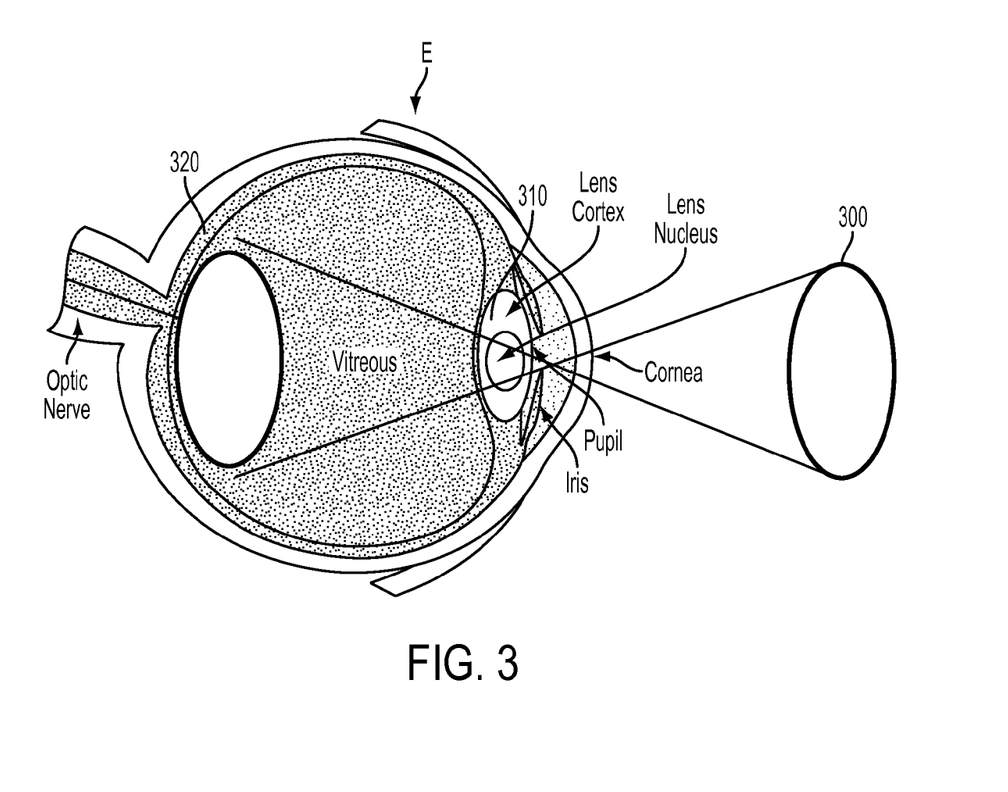
FIG. 3 is an exemplary cross-section of a patient eye.

FIG. 3 shows in general the light path and scope of the path 300 for an eye E. Typically, most of the light goes around the central nucleus of lens 310 of the eye E and is projected onto the eye's retina 320. The scope 300 shows the general range the focus of the eye E may travel, causing the eye E to change its position. As mentioned above, it may be desirable to cause the eye to fixate at one particular point, thereby fixating its position. However, during surgery, that desired position may shift. Or, the particular point that causes the eye to fixate at a particular position may shift. For example, lens ablation during cataract surgery may cause the eye to lose its focus on any particularly fixed point.

Figure 4:
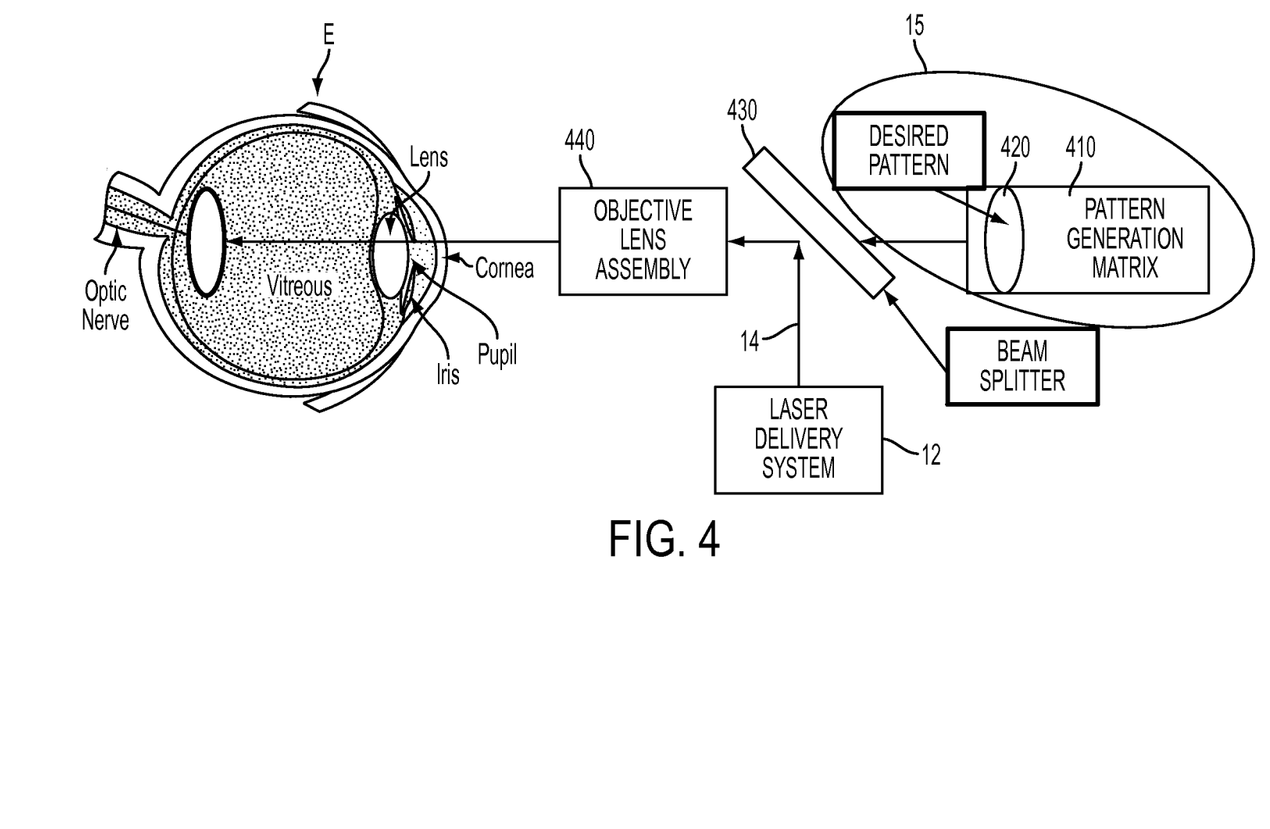
FIG. 4 is an illustration of light path in conjunction with a fixation system according to a preferred embodiment of the present invention.

Turning to FIG. 4, an exemplary patient fixation system 15 with delivery optics 16 is illustrated for use to align the eye to a particular position. In general, the fixation system 15 includes one or more configurable and multi-color light emitting diodes (LEDs) optically positioned in front of/above the patient in the form of patterns. The fixation system 15 also includes a pattern generation matrix 410 which is used to statically or dynamically generate, adjust, change, or re-position one or more desired patterns 420. The generated desired patterns 420 and/or fixation maps may be stored in storage media 29 and retrieved for use. A beam splitter 430 and an objective lens assembly 340, which are typically part of the delivery optics 16, align the LED light output of the desired patterns on the eye E. The pattern generation matrix 410 may be controlled automatically by program code or software, or by using input from a system operator (or surgeon) utilizing one or more user interface input devices 62. The fixation system 15 may work independently or in conjunction with an eye tracking system (not shown) of the laser system 10. In one embodiment, the program code or software periodically or continuously monitors information received from the eye E or from the eye tracking system. Based on this information, the illumination points may be dynamically adjusted, changed, or re-positioned by, for example, applying different patterns or varying distances, or based on timing, motion of light source, on frequency of blinking of the eye, or cornea sensitivity level, or in synchronization with the surgical procedure, or in response to or synchronization with any other information received from the eye, and so on.

Figure 5:
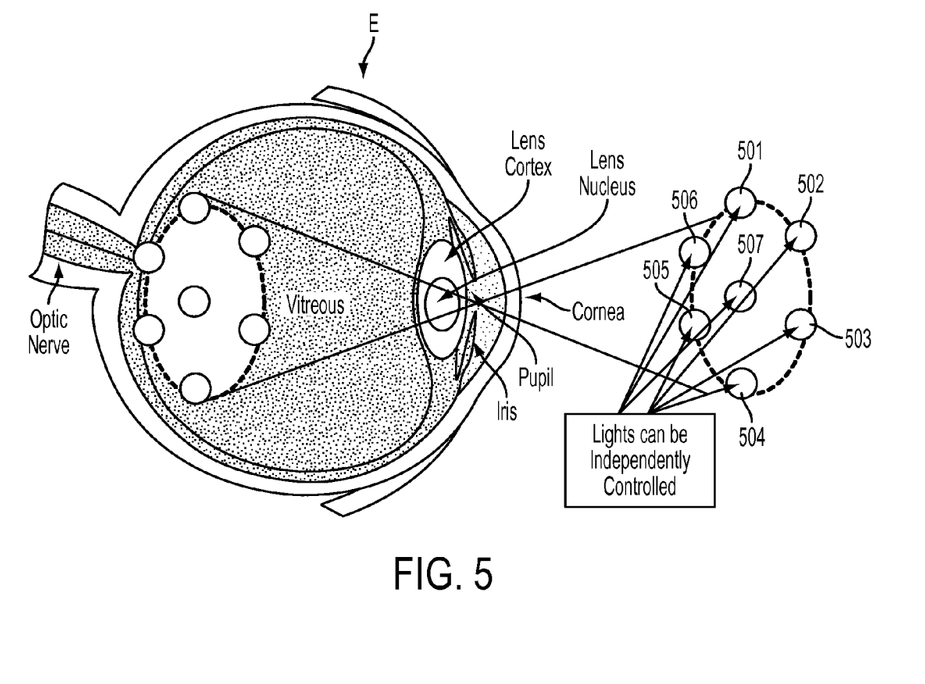
FIG. 5 is an illustration of light path for exemplary target patterns according to a preferred embodiment of the present invention.

FIG. 5 illustrates the operation of one exemplary embodiment. In this example, a plurality of illumination points 501-507 is generated. Each of the illumination points 501-507 may be generated automatically and individually, using the pattern generation matrix 410 to form an exemplary desired pattern 420. Alternatively, each of the illumination points 501-507 may be generated using input from a system operator utilizing one or more user interface input devices 62. During the diagnostic or surgical operation, the illumination points 501-507 may then be controlled, e.g., dynamically adjusted, changed, or re-positioned to cause the patient to fixate its eye E at a desired position. The adjustments, changes, or re-positions may be done automatically, e.g., based on the response to an eye tracking system or by using input from a system operator.

Figure 6:
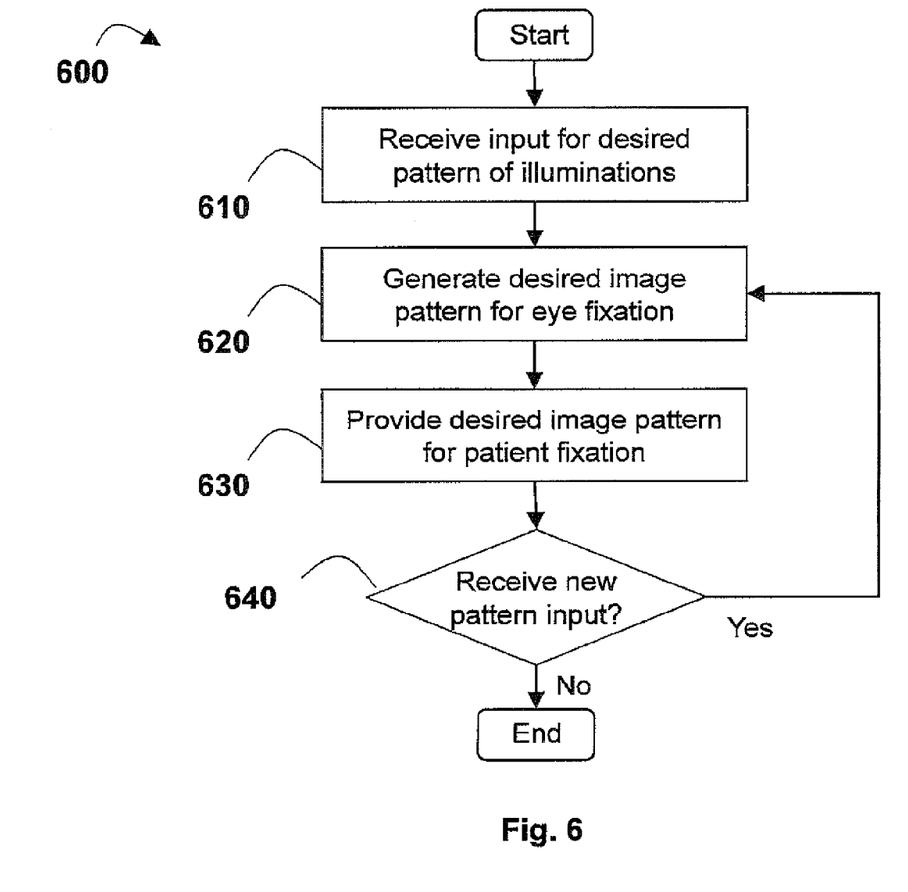
FIG. 6 is a flowchart illustrating a process according to a preferred embodiment of the present invention.

Turning to FIG. 6, a process 600 according to an embodiment of the invention is shown. The fixation system 15 receives input from the computer system 22 for the generation of a desired pattern of one or more illumination points (Action Block 610). Based on the received input, the fixation system 15 generates a first desired image pattern (Action Block 620), and provides the pattern of illumination points to the laser system 10 for delivery to the patient eye E (Action Block 630). During the diagnostic or surgical procedure, the fixation system 15 may receive further input from the computer system 22, for example, the fixation system is notified that the current one or more patterns may need to be adjusted, changed or re-positioned to cause the patient to change its current eye position based on user and/or system feedback (Decision Block 640). For example, a patient's lens may have been ablated, causing the patient to lose focus at the desired position. The operator and/or eye tracking system may detect this and shift the pattern to cause the patient to focus its eye back at the desired position. If so, the fixation system 15 generates another desired image pattern (Action Block 620) for use.

In the current state of the art, all that current fixation systems typically provide is a single illumination point at a fixed location provided by a fixed light source. For procedures and situations where the patient's focal point shifts or his or her ability to focus changes, such current systems do not accommodate such situations and conditions. The systems described above, however, do address dynamic situations by not only enabling the operator to shift the location of the illumination point, but also to add illumination points, create patterns, and change the light source, such as the color, brightness, size, and duration (e.g., blinking lights may be used). Each of these elements, in combination, or individually, may facilitate the ability to have the patient focus his or her eye(s) at a desired location despite the change in the surrounding conditions.

In the foregoing specification, the invention has been described with reference to specific embodiments thereof. It will, however, be evident that various modifications and changes may be made thereto without departing from the broader spirit and scope of the invention. For example, the reader is to understand that the specific ordering and combination of process actions described herein is merely illustrative, and the invention may appropriately be performed using different or additional process actions, or a different combination or ordering of process actions. For example, this invention is particularly suited for laser-based ophthalmic surgical systems, however, the invention can be used for any ophthalmic surgical system.

Additionally and obviously, features may be added or subtracted as desired. Accordingly, the invention is not to be restricted except in light of the attached claims and their equivalents.

What is claimed is:

1. An ophthalmic laser-based treatment system comprising:
   a laser delivery system for delivering a pulsed laser beam to an eye;
   an eye fixation system positioned proximate to the laser delivery system and configured to cause the eye to be fixated at a desired position, the eye fixation system including one or more light sources generating one or more light beams which are different from the pulsed laser beam, wherein the laser delivery system delivers the one or more light beams from the eye fixation system to the eye; and
   an eye fixation adjustment system configured to dynamically adjust the eye fixation system to change one or more of: location, number of beams, pattern, color, brightness, size, and duration, of the one or more light beams in response to an input during an ophthalmic laser treatment procedure.

2. The system of claim 1, wherein the one or more light sources of the eye fixation system generate one or more illuminated points at different locations within the eye's optical path, and the eye fixation adjustment system includes a controller for controlling the location of the one or more illuminated points.

3. The system of claim 2, wherein the eye fixation adjustment system is configured to cause the eye fixation system to generate a plurality of illuminate points according to a pattern and to dynamically adjust the pattern.

4. The system of claim 2, wherein the eye fixation adjustment system is operatively coupled to an eye tracking system.

5. The system of claim 2, wherein the eye fixation adjustment system is operatively coupled to a manually driven controller.

* * * * *